US012788737B2

(12) United States Patent
Mardinoglu et al.

(10) Patent No.: US 12,788,737 B2
(45) Date of Patent: Nov. 10, 2026

(54) SUBSTANCES FOR TREATMENT OF HYPERURICAEMIA

(71) Applicant: SCANDIBIO THERAPEUTICS AB, Solna (SE)

(72) Inventors: Adil Mardinoglu, Gothenburg (SE); Jan Borén, Gothenburg (SE); Mathias Uhlén, Lidingö (SE)

(73) Assignee: SCANDIBIO THERAPEUTICS AB, Solna (SE)

( * ) Notice: Subject to any disclaimer, the term of this patent is extended or adjusted under 35 U.S.C. 154(b) by 704 days.

(21) Appl. No.: 18/252,843

(22) PCT Filed: Nov. 16, 2021

(86) PCT No.: PCT/EP2021/081847

§ 371 (c)(1),
(2) Date: May 12, 2023

(87) PCT Pub. No.: WO2022/101501

PCT Pub. Date: May 19, 2022

(65) Prior Publication Data

US 2024/0000737 A1 Jan. 4, 2024

(30) Foreign Application Priority Data

Nov. 16, 2020 (EP) .................................... 20207916

(51) Int. Cl.

*A61K 31/197* (2006.01)
*A61K 31/205* (2006.01)
*A61K 31/4412* (2006.01)
*A61K 31/455* (2006.01)
*A61K 31/706* (2006.01)
*A61K 31/7076* (2006.01)
*A61P 13/02* (2006.01)

(52) U.S. Cl.

CPC .......... *A61K 31/197* (2013.01); *A61K 31/205* (2013.01); *A61K 31/4412* (2013.01); *A61K 31/455* (2013.01); *A61K 31/706* (2013.01); *A61K 31/7076* (2013.01); *A61P 13/02* (2018.01)

(58) Field of Classification Search

None
See application file for complete search history.

(56) References Cited

U.S. PATENT DOCUMENTS

| | | | | |
|---|---|---|---|---|
| 5,728,678 A * | 3/1998 | Trimbo | A61P 15/00 514/561 |
| 2008/0249168 A1 | 10/2008 | Gu | |
| 2020/0069624 A1* | 3/2020 | Reiner | A61K 45/06 |

FOREIGN PATENT DOCUMENTS

| | | |
|---|---|---|
| EP | 3677263 A1 | 7/2020 |
| WO | 2016158212 A1 | 10/2016 |
| WO | 2018117954 A1 | 6/2018 |

OTHER PUBLICATIONS

Maurer et al. Dose Predictions for Drug Design. Journal of Medicinal Chemistry. vol. 63, Issue 12. Published Jan. 2020. (Year: 2020).*
Mountainside Medical Equipment. Nutrition Delivery Methods. Retrieved from the Internet on Oct. 20, 2025, https://www.mountainside-medical.com/blogs/medical-supplies/51453892-nutrition-delivery-methods?srsltid=AfmBOorzXEN-oQWc6d9kzdcU5Z55g_br1F0oumDv-kGiZRopfsfZC8IE. Published 2012. (Year: 2012).*
PubChem. Nicotinamide. Retrieved from the Internet on Oct. 20, 2025, pubchem.ncbi.nlm.nih.gov/compound/936#section=Depositor-Supplied-Synonyms&fullscreen=true (Year: 2025).*
Breyer MD, Susztak K. The next generation of therapeutics for chronic kidney disease. Nat Rev Drug Discov. Aug. 2016;15(8):568-88. doi: 10.1038/nrd.2016.67. Epub May 27, 2016. (Year: 2016).*
Lin MY, Chiu YW, Lin YH, Kang Y, Wu PH, Chen JH, Luh H, Hwang SJ, On Behalf Of The iH Research Group. Kidney Health and Care: Current Status, Challenges, and Developments. J Pers Med. Apr. 22, 2023;13(5):702. (Year: 2023).*
"Extended European Search Report corresponding to European Application No. 20207916.6 dated May 11, 2021".
"International Search Report and Written Opinion corresponding to International Application No. PCT/EP2021/081847 mailed Feb. 23, 2022".
Sochman, Jan , et al., "Prevention of contrast agent-induced renal impairment in patients with chronic renal insufficiency and heart disease by high-dose intravenous N-acetylcysteine: a pilot-ministudy", Kardiol Pol 64 (6):559-564 (Jan. 1, 2006).
"Deoxycarnitine", Biosynth, https://www.biosynth.com/p/XD182598/407-64-7-deoxycarnitine (last updated in Jun. 2026) 1 page.
"A Look at Carnitine", SpectraCell Laboratories https://www.spectracell.com/blog/a-look-at-carnitine (Apr. 14, 2014) 2 pages.
"Definition of Gout", Am Coll Rheumatology, https://rheumatology.org/patients/gout (last updated in Feb. 2025) 1 page.
"Hyperuricemia (High Uric Acid Level)", Cleveland Clinic, https://my.clevelandclinic.org/health/diseases/17808-hyperuricemia-high-uric-acid-level (last updated in Jul. 2023) 5 pages.
Denu, "Vitamins and Aging: Pathways to NAD+ Synthesis", Cell 129(3):453-454 (May 4, 2007).
Moffett, et al., "Quinolinate as a Marker for Kynurenine Metabolite Formation and the Unresolved Question of NAD + Synthesis During Inflammation and Infection", Frontiers in Immunology 11:Article 31 (Feb. 2020) 27 pages.

(Continued)

*Primary Examiner* — Lauren Wells
(74) *Attorney, Agent, or Firm* — Myers Bigel, P.A.

(57) ABSTRACT

A composition for use in a therapeutic method of treatment or prevention of hyperuricaemia, gout and/or renal impairment, said composition comprising: A) serine, glycine, betaine, N-acetylglycine, N-acetylserine, dimethylglycine, sarcosine and/or phosphoserine; B) N-acetyl cysteine, cysteine and/or cystine; C) optionally carnitine, deoxycarnitine, gamma-butyrobetaine, 4-trimethylammoniobutanal, 3-hydroxy-N6,N6,N6-trimethyl-L-lysine, N6,N6,N6-trimethyl-L-lysine and/or lysine; and D) nicotinamide riboside, quinolinate, deamino-NAD+, nicotinate D-ribonucleotide, nicotinamide D-ribonucleotide, nicotinate D-ribonucleoside, nicotinamide and/or nicotinate.

26 Claims, 5 Drawing Sheets

(56) References Cited

OTHER PUBLICATIONS

Sansone, et al., “Getting a Knack for NAC: N-Acetyl-Cysteine”, Innov Clin Neurosci. 8(1):10-14 (Jan. 2011).
“Cysteine (and Cystine)”, Chemtymology https://chemtymology.co.uk/2020/11/27/cysteine-and-cystine/ (Nov. 27, 2020) 3 pages.
Zhang, et al., “The glycine transport inhibitor sarcosine is an NMDA receptor co-agonist that differs from glycine”, J Physiol 587(13):3207-3220 (May 11, 2009).
Zhou, et al., “Serine-to-glycine ratios in low-protein diets regulate intramuscular fat by affecting lipid metabolism and myofiber type transition in the skeletal muscle of growing-finishing pigs”, Animal Nutrition 7:384-392 (Mar. 2021).
“Tips to Naturally Reduce Uric Acid and How to Fit them into your Routine”, Healthline, https://www.healthline.com/health/how-to-reduce-uric-acid (last updated on Feb. 6, 2024) 6 pages.

* cited by examiner

SUBSTANCES FOR TREATMENT OF HYPERURICAEMIA

STATEMENT OF PRIORITY

This application is a 35 U.S.C. § 371 national phase application of PCT Application No. PCT/EP2021/081847 filed Nov. 16, 2021, which claims priority to European Application No. 20207916.6, filed Nov. 16, 2020, the entire contents of each of which are incorporated by reference herein.

TECHNICAL FIELD

The present disclosure relates to the field of treatment of hyperuricaemia.

BACKGROUND

Hyperuricaemia is commonly defined as a serum uric acid concentration above 6.8 mg/dl, which level is based on the in vivo solubility of uric acid. Above 6.8 mg/dl, crystal deposition may occur. However, it should be noted that alternative definitions of hyperuricemia are sometimes applied (Benn et al. (2018) *Front. Med.* 5:160).

Gout is the most common inflammatory arthritis. It occurs when the supersaturated uric acid levels of hyperuricaemia lead to the formation and deposition of monosodium urate crystals in and around the joints. Recent reports of the prevalence and incidence of gout vary widely according to the population studied and methods employed, but range from a prevalence of <1% to 6.8% and an incidence of 0.58-2.89 per 1,000 person-years. Gout is more prevalent in men than in women. Despite rising prevalence and incidence, suboptimal management of gout continues in many countries. Typically, only a third to half of patients with gout receive urate-lowering therapy and fewer than a half of patients adhere to treatment (Dehlin et al. (2020) *Nat Rev Rheumatol* 16, 380-390).

Further, hyperuricaemia has been associated with impaired renal function (Tanaka et al. (2017) *PLoS ONE* 12(7)).

SUMMARY

An aim of the present disclosure is to provide for the treatment or prevention of hyperuricaemia, gout and/or renal impairment.

In the Examples section below, it is shown that the administration of a mixture of the substances serine, N-acetyl cysteine (NAC), L-carnitine and nicotinamide riboside (NR) lowers the serum levels of uric acid and creatinine (an indicator of kidney health) in human subjects.

Considering metabolic pathways, the present inventors have identified the following alternatives to the above-mentioned substances:

| Substance | Alternatives |
|---|---|
| serine | glycine, betaine, N-acetylglycine, N-acetylserine, dimethylglycine, sarcosine and/or phosphoserine |
| NAC | Cysteine and/or cystine |
| L-carnitine | deoxycarnitine, gamma-butyrobetaine, 4-trimethylammoniobutanal, 3-hydroxy-N6,N6,N6-trimethyl-L-lysine, N6,N6,N6-trimethyl-L-lysine and/or lysine |
| NR | quinolinate, deamino-NAD+, nicotinate D-ribonucleotide, nicotinamide D-ribonucleotide, nicotinate D-ribonucleoside, nicotinamide and/or nicotinate |

To obtain the therapeutic effect, it is not necessary to always include all four substances. The inventors have however identified serine (or one or more of its alternatives) and NR (or one or more of its alternatives) as the most important substances. Further, the inventors have found that the optimal daily molar dose is higher for serine than for NR.

Accordingly, the following itemized listing of embodiments of the present disclosure is provided:

1. A composition for use in a therapeutic method of treatment or prevention of hyperuricaemia, gout and/or renal impairment, said composition comprising:

A) serine, glycine, betaine, N-acetylglycine, N-acetylserine, dimethylglycine, sarcosine and/or phosphoserine;

B) N-acetyl cysteine, cysteine and/or cystine;

C) optionally carnitine, deoxycarnitine, gamma-butyrobetaine, 4-trimethylammoniobutanal, 3-hydroxy-N6,N6,N6-trimethyl-L-lysine, N6,N6,N6-trimethyl-L-lysine and/or lysine; and D) nicotinamide riboside, quinolinate, deamino-NAD+, nicotinate D-ribonucleotide, nicotinamide D-ribonucleotide, nicotinate D-ribonucleoside, nicotinamide and/or nicotinate.

2. The composition for use according to item 1, wherein the molar ratio of A) to B) is between 20:1 and 1:4, such as 16:1 and 1:4, such as between 12:1 and 1.5:1, preferably between 10:1 and 3:1.
3. The composition for use according to any one of the preceding items, wherein the molar ratio of A) to C) is between 150:1 and 1:1, such as between 100:1 and 2:1, preferably between 30:1 and 3:1, more preferably between 15:1 and 4:1.
4. The composition for use according to any one of the preceding items, wherein the molar ratio of A) to D) is between 250:1 and 1.5:1, such as 150:1 and 3:1, preferably between 90:1 and 10:1, more preferably between 50:1 and 20:1.
5. The composition for use according to any one of the preceding items, wherein A) is serine, preferably L-serine.
6. The composition for use according to any one of the preceding items, wherein B) is N-acetyl cysteine or cysteine.
7. The composition for use according to any one of the preceding items, wherein C) is carnitine.
8. The composition for use according to any one of the preceding items, wherein D) is nicotinamide riboside or nicotinamide D-ribonucleotide.
9. The composition for use according to any one of the preceding items, which is powderous mixture.
10. The composition for use according to any one of the preceding items, wherein said method is carried out on a human subject.
11. The composition for use according to any one of the preceding items, wherein said method comprises oral administration of the composition.
12. The composition for use according to any one of the preceding items, wherein said method comprises administration of:

A) in a dose of 0.48-24 mmol/kg/day, such as 0.48-4.8 mmol/kg/day, such as 1.8-4.8 mmol/kg/day, such as 2.9-4.7 mmol/kg/day;

B) in a dose of 0.31-3.05 mmol/kg/day, such as 0.31-1.84 mmol/kg/day, such as 0.40-1.23 mmol/kg/day;

optionally C) in a dose of 0.100-2.50 mmol/kg/day, such as 0.200-2.00 mmol/kg/day, such as 0.230-1.00 mmol/kg/day, such as 0.300-0.800 mmol/kg/day; and D) in a dose of 0.015-0.39 mmol/kg/day, such as 0.030-0.31 mmol/kg/day, such as 0.040-0.20 mmol/kg/day.

13. The composition for use according to any one of the preceding items, wherein said method comprises administration of:

A) in a dose of 100-600 mmol/day, such as 150-450 mmol/day, such as 170-350 mmol/day;

B) in a dose of 12-100 mmol/day, such as 16-75 mmol/day, such as 20-50 mmol/day;

optionally C) in a dose of 12-100 mmol/day, such as 16-75 mmol/day, such as 20-50 mmol/day; and D) in a dose of 3-20 mmol/day, such as 3-15 mmol/day, such as 4-10 mmol/day.

14. Substances comprising

A) serine, glycine, betaine, N-acetylglycine, N-acetylserine, dimethylglycine, sarcosine and/or phosphoserine, B) N-acetyl cysteine, cysteine and/or cystine, C) optionally carnitine, deoxycarnitine, gamma-butyrobetaine, 4-trimethylammoniobutanal, 3-hydroxy-N6,N6,N6-trimethyl-L-lysine, N6,N6,N6-trimethyl-L-lysine and/or lysine and D) nicotinamide riboside, quinolinate, deamino-NAD+, nicotinate D-ribonucleotide, nicotinamide D-ribonucleotide, nicotinate D-ribonucleoside, nicotinamide and/or nicotinate for simultaneous, separate or sequential use in a therapeutic method of treatment or prevention of hyperuricaemia, gout and/or renal impairment.

15. Substances for use according to item 14, wherein the molar ratio of A) to B) is between 20:1 and 1:4, such as 16:1 and 1:4, such as between 12:1 and 1.5:1, preferably between 10:1 and 3:1.

16. Substances for use according to any one of the preceding items 14-15, wherein the molar ratio of A) to C) is between 150:1 and 1:1, such as between 100:1 and 2:1, preferably between 30:1 and 3:1, more preferably between 15:1 and 4:1.

17. Substances for use according to any one of the preceding items 14-16, wherein the molar ratio of A) to D) is between 250:1 and 1.5:1, such as 150:1 and 3:1, preferably between 90:1 and 10:1, more preferably between 50:1 and 20:1.

18. Substances for use according to any one of the preceding items 14-17, wherein A) is serine, preferably L-serine.

19. Substances for use according to any one of the preceding items 14-18, wherein B) is N-acetyl cysteine or cysteine.

20. Substances for use according to any one of the preceding items 14-19, wherein C) is carnitine.

21. Substances for use according to any one of the preceding items 14-20, wherein D) is nicotinamide riboside or nicotinamide D-ribonucleotide.

22. Substances for use according to any one of the preceding items 14-21, wherein the method is carried out on a human subject.

23. Substances for use according to any one of the preceding items 14-22, wherein said method comprises oral administration of the substances.

24. Substances for use according to any one of the preceding items 14-23, wherein said method comprises administration of:

A) in a dose of 0.48-24 mmol/kg/day, such as 0.48-4.8 mmol/kg/day, such as 1.8-4.8 mmol/kg/day, such as 2.9-4.7 mmol/kg/day;

B) in a dose of 0.31-3.05 mmol/kg/day, such as 0.31-1.84 mmol/kg/day, such as 0.40-1.23 mmol/kg/day;

optionally C) in a dose of 0.100-2.50 mmol/kg/day, such as 0.200-2.00 mmol/kg/day, such as 0.230-1.00 mmol/kg/day, such as 0.300-0.800 mmol/kg/day; and D) in a dose of 0.015-0.39 mmol/kg/day, such as 0.030-0.31 mmol/kg/day, such as 0.040-0.20 mmol/kg/day.

25. Substances for use according to any one of the preceding items 14-24, wherein said method comprises administration of:

A) in a dose of 100-600 mmol/day, such as 150-450 mmol/day, such as 170-350 mmol/day;

B) in a dose of 12-100 mmol/day, such as 16-75 mmol/day, such as 20-50 mmol/day;

optionally C) in a dose of 12-100 mmol/day, such as 16-75 mmol/day, such as 20-50 mmol/day; and D) in a dose of 3-20 mmol/day, such as 3-15 mmol/day, such as 4-10 mmol/day.

26. Substances for use according to any one of the preceding items 14-25, wherein:

A) is serine;

B) is N-acetyl cysteine or cysteine;

C) is carnitine; and

D) is nicotinamide riboside or nicotinamide D-ribonucleotide.

27. A method of treatment or prevention of hyperuricaemia, gout and/or renal impairment, comprising administration of:

A) serine, glycine, betaine, N-acetylglycine, N-acetylserine, dimethylglycine, sarcosine and/or phosphoserine;

B) N-acetyl cysteine, cysteine and/or cystine;

C) optionally carnitine, deoxycarnitine, gamma-butyrobetaine, 4-trimethylammoniobutanal, 3-hydroxy-N6,N6,N6-trimethyl-L-lysine, N6,N6,N6-trimethyl-L-lysine and/or lysine; and D) nicotinamide riboside, quinolinate, deamino-NAD+, nicotinate D-ribonucleotide, nicotinamide D-ribonucleotide, nicotinate D-ribonucleoside, nicotinamide and/or nicotinate.

28. The method of item 27, wherein the administration of A), B), optionally C) and D) is simultaneous, separate or sequential.

29. The method of any one of items 27-28, wherein A), B), optionally C) and D) are contained in a composition that is administered to the subject.

30. The method of any one of items 27-29, wherein the molar ratio of A) to B) is between 20:1 and 1:4, such as 16:1 and 1:4, such as between 12:1 and 1.5:1, preferably between 10:1 and 3:1.

31. The method of any one of items 27-30, wherein the molar ratio of A) to C) is between 150:1 and 1:1, such as between 100:1 and 2:1, preferably between 30:1 and 3:1, more preferably between 15:1 and 4:1.

32. The method of any one of items 27-31, wherein the molar ratio of A) to D) is between 250:1 and 1.5:1, such as 150:1 and 3:1, preferably between 90:1 and 10:1, more preferably between 50:1 and 20:1.

33. The method of any one of items 27-32, wherein A) is serine, preferably L-serine.

34. The method of any one of items 27-33, wherein B) is N-acetyl cysteine or cysteine.

35. The method of any one of items 27-34, wherein C) is carnitine.

36. The method of any one of items 27-35, wherein D) is nicotinamide riboside or nicotinamide D-ribonucleotide.

37. The method of any one of items 27-36, wherein said method is carried out on a human subject.

38. The method of any one of items 27-37, wherein said method comprises oral administration of the substances.

39. The method of any one of items 27-38, wherein said method comprises administration of:

A) in a dose of 0.48-24 mmol/kg/day, such as 0.48-4.8 mmol/kg/day, such as 1.8-4.8 mmol/kg/day, such as 2.9-4.7 mmol/kg/day;

B) in a dose of 0.31-3.05 mmol/kg/day, such as 0.31-1.84 mmol/kg/day, such as 0.40-1.23 mmol/kg/day;

optionally C) in a dose of 0.100-2.50 mmol/kg/day, such as 0.200-2.00 mmol/kg/day, such as 0.230-1.00 mmol/kg/day, such as 0.300-0.800 mmol/kg/day; and D) in a dose of 0.015-0.39 mmol/kg/day, such as 0.030-0.31 mmol/kg/day, such as 0.040-0.20 mmol/kg/day.

40. The method of any one of items 27-39, wherein said method comprises administration of:

A) in a dose of 100-600 mmol/day, such as 150-450 mmol/day, such as 170-350 mmol/day;

B) in a dose of 12-100 mmol/day, such as 16-75 mmol/day, such as 20-50 mmol/day;

optionally C) in a dose of 12-100 mmol/day, such as 16-75 mmol/day, such as 20-50 mmol/day; and D) in a dose of 3-20 mmol/day, such as 3-15 mmol/day, such as 4-10 mmol/day.

BRIEF DESCRIPTION OF THE DRAWINGS

In the figures, "ns" represents a non-significant difference. "*" represents a significant difference. "" represents a more significant difference. "*" represents an even more significant difference.

For each of the patients that came in for the clinical visit two weeks into the clinical study.

DETAILED DESCRIPTION

Figure 1:
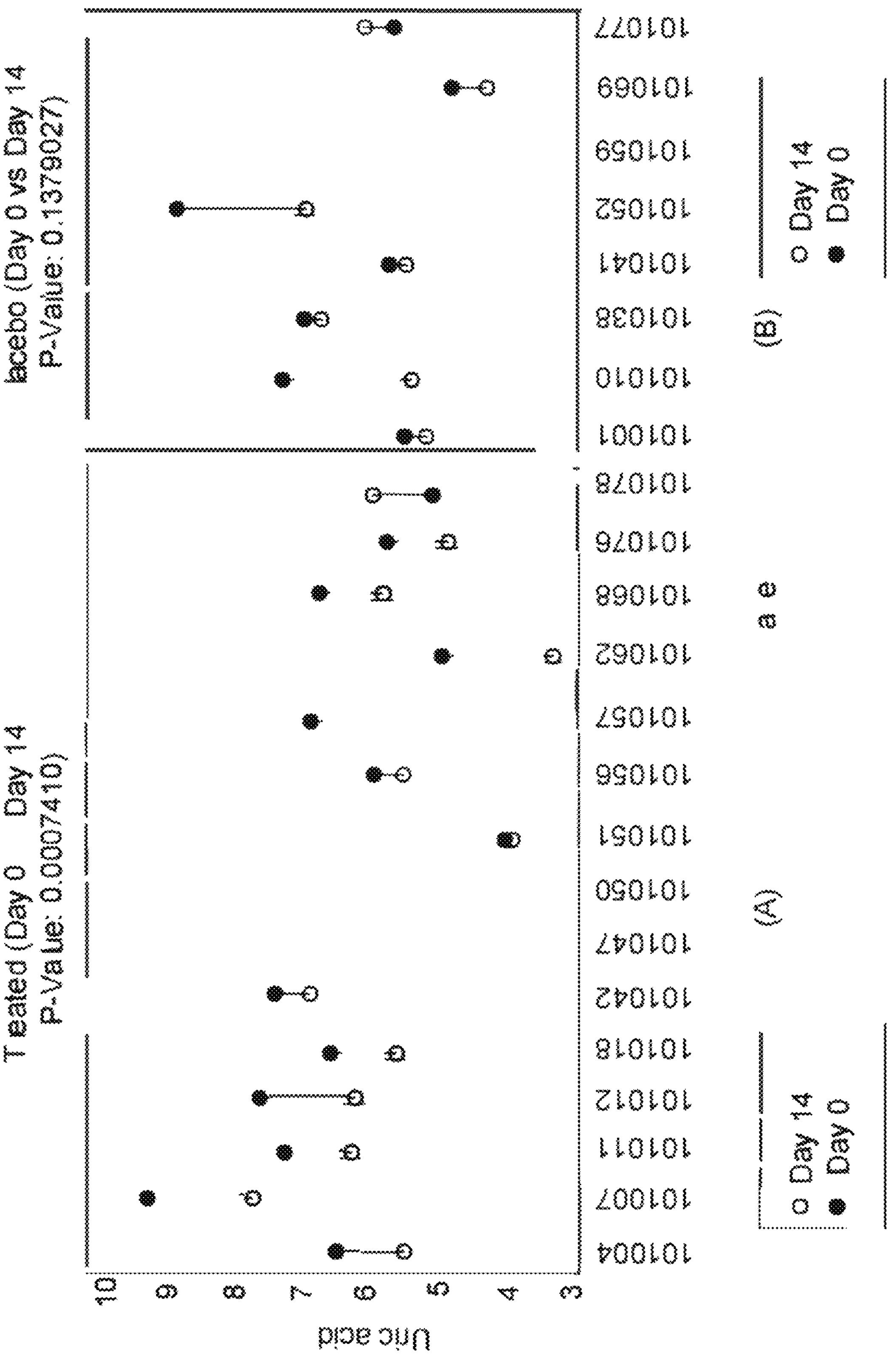
FIG. 1 shows the uric acid levels (mg/dl) at baseline (Day 0) and after two weeks (Day 14) of oral administration of either the mixture of the four substances (A) or placebo (B).

As a first aspect of the present disclosure, there is provided a composition for use in a therapeutic method of treatment or prevention of hyperuricaemia, gout and/or renal impairment. In an embodiment, the composition is for use in a therapeutic method of treatment or prevention of hyperuricaemia or gout.

In the context of the present disclosure, hyperuricaemia is defined as a serum uric acid concentration above 6.8 mg/dl. Alternatively, hyperuricaemia is defined as a serum uric acid concentration above 6 mg/dl in women and above 7 mg/dl in men.

The composition comprises:

A) serine, glycine, betaine, N-acetylglycine, N-acetylserine, dimethylglycine, sarcosine and/or phosphoserine;

B) optionally N-acetyl cysteine, cysteine and/or cystine;

C) optionally carnitine, deoxycarnitine, gamma-butyrobetaine, 4-trimethylammoniobutanal, 3-hydroxy-N6,N6,N6-trimethyl-L-lysine, N6,N6,N6-trimethyl-L-lysine and/or lysine; and D) nicotinamide riboside, quinolinate, deamino-NAD+, nicotinate D-ribonucleotide, nicotinamide D-ribonucleotide, nicotinate D-ribonucleoside, nicotinamide and/or nicotinate.

Preferably, the composition comprises A), B), D) and optionally C).

In a variant of the first aspect, the composition comprises A), B), C) and optionally D).

In group A), serine and glycine are preferred. The most preferred substance in group A) is serine, which is typically provided as L-serine.

In group B), N-acetyl cysteine (NAC) and cysteine are preferred. The most preferred substance in group B) is NAC.

The substance of group C) is preferably carnitine, optionally in the form of a carnitine salt, such as carnitine tartrate. Most preferably, the substance of group C) is L-carnitine, optionally in the form of a L-carnitine salt, such as L-carnitine tartrate.

The substance of group D) is preferably nicotinamide riboside (NR), nicotinamide D-ribonucleotide or nicotinate. In the art, nicotinamide D-ribonucleotide is also referred to as nicotinamide mononucleotide (NMN). NR is typically provided as a salt, preferably NR chloride. Nicotinate may be provided as inositol hexanicotinate, which is also referred to as flush free niacin since it allows slower absorption.

The substance(s) of group A) is/are preferably included in a higher molar amount than the substance(s) of group D). When efficacy and toxicity also considered, the molar ratio of A) to D) is normally between 250:1 and 1.5:1 and typically between 150:1 and 3:1. Preferably, the molar ration is between 90:1 and 10:1, more preferably between 50:1 and 20:1.

The molar ratio of A) to B), considering efficacy and toxicity, is typically between 20:1 and 1:4, such as between 16:1 and 1:4, such as between 16:1 and 1.5:1, preferably between 12:1 and 1.5:1 and more preferably between 10:1 and 3:1.

In embodiments including the substance(s) of group C), the molar ratio of A) to C), considering efficacy and toxicity, is normally between 150:1 and 1:1, typically between 100:1 and 2:1, preferably between 30:1 and 3:1, more preferably between 15:1 and 4:1.

The above ratios entail that a patient consuming the composition can obtain appropriate doses of the respective substances.

In one embodiment, the composition of the first aspect is a solid, such as a solid powder. Such a powder can be mixed with water, e.g. by the patient/consumer, a nurse or a physician. In another embodiment, the composition of the first aspect is an aqueous solution or suspension ("cocktail"), which facilitates convenient oral administration. Such an aqueous solution or suspension is preferably ready to drink.

In a particularly preferred embodiment of the first aspect, the composition is a powder comprising:

A) serine;
B) N-acetyl cysteine and/or cysteine;
C) carnitine; and
D) NR and/or NMN, wherein
the molar ratio of A) to B) is between 16:1 and 1.5:1, preferably between 10:1 and 3:1,
the molar ratio of A) to C) is between 100:1 and 2:1, preferably between 30:1 and 3:1, more preferably between 15:1 and 4:1; and
the molar ratio of A) to D) is between 150:1 and 3:1, preferably between 90:1 and 10:1, more preferably between 50:1 and 20:1.

In another particularly preferred embodiment of the first aspect, the composition is a powder comprising:

A) serine;
B) N-acetyl cysteine and/or cysteine;
C) optionally carnitine; and
D) nicotinamide riboside, wherein
the molar ratio of A) to D) is between 90:1 and 10:1, preferably between 50:1 and 20:1, more preferably between 44:1 and 24:1.

In embodiments of the solution or suspension according to the first aspect:

the concentration of A) is typically 0.20-2.4 mmol/ml, preferably 0.40-2.4 mmol/ml and more preferably 0.60-2.4 mmol/ml;
the concentration of B) is normally 0.09-0.90 mmol/ml, typically 0.09-0.54 mmol/ml, preferably 0.11-0.40 mmol/ml and more preferably 0.013-0.30 mmol/ml; and/or
the concentration of D) is typically 0.006-0.12 mmol/ml, preferably 0.012-0.08 mmol/ml and more preferably 0.018-0.07 mmol/ml.

When C) is included in the solution or suspension according to the first aspect, its concentration is normally 0.009-0.38 mmol/ml, typically 0.009-0.19 mmol/ml, preferably 0.016-0.16 mmol/ml and more preferably 0.028-0.12 mmol/ml.

The solution or suspension of the first aspect may be provided in a package for convenient handling and distribution. Further, the volume of such a package may be such that drinking the whole contents of the package at once or during a single day results in oral administration of appropriate doses of the substances in the solution or suspension. In one embodiment, the volume of the package is 25-1000 ml. The volume is preferably 50-500 ml. When it is intended that the consumer/patient shall drink more than one package per day, the volume is typically relatively low, such as 25-500 ml, preferably 25-400 ml.

In one embodiment, the packaged solution or suspension comprises 48-478 mmol of A). Thereby, the dose of A) is effective, but not toxic. In a preferred embodiment, A) is serine in an amount of 5-50 g, more preferably 10-50 g.

In an alternative of complimentary embodiment, the packaged solution or suspension comprises 2.0-39.2 mmol of D) when D) is NR and 2.0-196 mmol of D) when D) is not NR. Thereby, the dose of D) is effective, but not toxic. In a preferred embodiment, D) is NR in an amount of 0.5-10 g, more preferably 1.0-6.0 g.

When the composition of the first aspect is a powder, it may also be packaged. As an example, the powder may be provided in unit dose packs. It follows from the discussion above that such a unit dose may comprise 48-478 mmol of A) and/or 2.0-39.2 mmol of D) when D) is NR and 2.0-196 mmol of D) when D) is not NR. Further, such as packed powder preferably comprises serine in an amount of 5-50 g and/or NR in an amount of 0.5-10 g. More preferably, such a packed powder comprises serine in an amount of 10-50 g and/or NR in an amount of 1.0-6.0 g.

The substances of the present disclosure are preferably a significant part of the composition of the first aspect. For example, the substances included in groups A)-D) may amount to at least 10%, such as at least 25%, such as at least 50% of the dry weight of the composition of the first aspect. In one embodiment, the weight of serine is at least 10%, such as at least 25%, such as at least 40% of the dry weight of the composition of the first aspect.

The composition of the first aspect may comprise one or more tasting agent(s), such as one or more sweetener(s) (e.g. sucralose) and/or one or more flavor agent(s). It may also comprise a lubricant, such as a polyethylene glycol lubricant (e.g. Polyglykol 8000 PF (Clariant)).

In an embodiment, the therapeutic method comprises oral administration of the composition.

The therapeutic method may for example comprise administration, such as oral administration, of:

A) in a dose of 0.48-24 mmol/kg/day, such as 0.48-4.8 mmol/kg/day, such as 1.8-4.8 mmol/kg/day, such as 2.9-4.7 mmol/kg/day;
B) in a dose of 0.31-3.05 mmol/kg/day, such as 0.31-1.84 mmol/kg/day, such as 0.40-1.23 mmol/kg/day;
optionally C) in a dose of 0.100-2.50 mmol/kg/day, such as 0.200-2.00 mmol/kg/day, such as 0.230-1.00 mmol/kg/day, such as 0.300-0.800 mmol/kg/day; and/or
D) in a dose of 0.015-1.96 mmol/kg/day, such as 0.015-0.39 mmol/kg/day, such as 0.030-0.31 mmol/kg/day, such as 0.040-0.20 mmol/kg/day, provided that the dose is not higher than 0.39 mmol/kg/day when D) is NR.

If the doses are not adjusted to the weight of the patient, the therapeutic method may for example comprise administration, such as oral administration, of:

A) in a dose of 100-600 mmol/day, such as 150-450 mmol/day, such as 170-350 mmol/day;
B) in a dose of 12-100 mmol/day, such as 16-75 mmol/day, such as 20-50 mmol/day; and/or
D) in a dose of 3-20 mmol/day, such as 3-15 mmol/day, such as 4-10 mmol/day.

Further, C) may be administrated in a dose of 12-100 mmol/day, such as 16-75 mmol/day, such as 20-50 mmol/day The daily dose may be reached by administrating one or more doses per day to the patient. In one embodiment, the number of daily doses is one, two or three. For example, the patient may consume a drink formed from the composition in powderous form one, two or three times per day. Each dose or drink preferably comprises no more than 4.78 mmol/kg of A).

The method of treatment may for example be carried out for a period of at least one week, such as at least two weeks, such as at least three weeks. In one embodiment, the method of treatment is carried out for a period of at 1-14 weeks, such as 3-12 weeks.

For the patient/consumer, it is not necessary to take the substances of the present disclosure simultaneously. A therapeutic effect can also be achieved if the substances are taken separately or sequentially, preferably within a day and more preferably within an hour.

Accordingly, as a second aspect of the present disclosure, there is provided substances comprising A) serine, glycine, betaine, N-acetylglycine, N-acetylserine, dimethylglycine, sarcosine and/or phosphoserine, B) N-acetyl cysteine, cysteine and/or cystine, C) optionally carnitine, deoxycarnitine, gamma-butyrobetaine, 4-trimethylammoniobutanal, 3-hydroxy-N6,N6,N6-trimethyl-L-lysine, N6,N6,N6-trimethyl-L-lysine and/or lysine and D) nicotinamide riboside, quinolinate, deamino-NAD+, nicotinate D-ribonucleotide, nicotinamide D-ribonucleotide, nicotinate D-ribonucleoside, nicotinamide and/or nicotinate for simultaneous, separate or sequential use in a therapeutic method of treatment or prevention of hyperuricaemia, gout and/or renal impairment.

The embodiments and examples of the first aspect apply to the second aspect mutatis mutandis.

As a third aspect of the present disclosure, there is provided a method of treatment or prevention of hyperuricaemia, gout and/or renal impairment, comprising administration of:

A) serine, glycine, betaine, N-acetylglycine, N-acetylserine, dimethylglycine, sarcosine and/or phosphoserine;

B) N-acetyl cysteine, cysteine and/or cystine;

C) optionally carnitine, deoxycarnitine, gamma-butyrobetaine, 4-trimethylammoniobutanal, 3-hydroxy-N6,N6,N6-trimethyl-L-lysine, N6,N6,N6-trimethyl-L-lysine and/or lysine; and D) nicotinamide riboside, quinolinate, deamino-NAD+, nicotinate D-ribonucleotide, nicotinamide D-ribonucleotide, nicotinate D-ribonucleoside, nicotinamide and/or nicotinate.

The embodiments and examples of the first and the second aspect apply to the third aspect mutatis mutandis.

The subject of the first, second and third aspect is preferably a human subject.

Example: Clinical Trial

Trial Design and Oversight

A randomized, placebo-controlled, phase 2 study was conducted. Patients were recruited between Jul. 1, 2019, and Sep. 30, 2020 at the Koç University Hospital, Istanbul, Turkey. The trial was conducted in accordance with Good Clinical Practice guidelines and the principles of the Declaration of Helsinki. Safety of the participants and evaluation of the benefit-risk balance was overseen by an independent external data monitoring committee. Written informed consent was obtained from all participants before the initiation of any trial-related procedures.

The main aim of the study was to establish metabolic improvements in NAFLD subjects by dietary supplementation with N-acetylcysteine (NAC), L-carnitine tartrate, nicotinamide riboside (NR) and serine. The subjects of the trial took a mixture of the substances or matching placebo as powder dissolved in water by mouth.

The investigational drug product (i.e. the mixture of the four substances) and the placebo was produced in Turkey according to GMP regulations by Pharmactive Company according to EU standards and packed according to GMP rules with the appropriate dosage. The investigational drug product and the placebo were produced as soluble powders and packed in 60 mL HDPE plastic bottles with screw caps. Investigational drug product and placebo were not identifiable from its packaging. Investigational drug product and placebo were dissolved by the subjects of the trial in 200 ml cold water before use.

Stability tests performed by RISE (Sweden) have shown that the powder mixture of the four substances is stable at 25° C. for at least twelve (12) months in the plastic bottles.

The powder mixture further comprised strawberry aroma.

The placebo was sorbitol (5 g) flavored with strawberry aroma and further comprising a coloring agent. Sorbitol is widely used due to its solubility in water and approved by the U.S. Food and Drug Administration (FDA).

Study Population

The study was first designed to include 45 participants. However, thirty-two subjects (male and female) were enrolled due to COVID-19 restrictions. The study population consisted of overweight and obese subjects diagnosed with NAFLD, but not with type 2 diabetes or dyslipidemia and not undergoing treatment with an anti-diabetic medication. Eligible subjects met all the inclusion criteria and none of the exclusion criteria. The inclusion criteria included body mass index>27 kg/m$^2$, triglycerides≤354 mg/dl, LDL cholesterol 175 mg/dl and increased hepatic fat (>5.5%). The exclusion criteria included carrier of the PNPLA3 I148M (homozygous for I148M), ALT or AST levels>3× UNL, received oral antidiabetics including metformin within 3 months. Randomization and blinding, interventions and follow-up The study subjects were randomized on a 2:1 basis to the mixture of the four substances or placebo. A web-based randomization system was used to assign a randomization code for each patient. An investigator or another responsible person at the investigational site was able to enter the web-based randomization system specific to the study through assigned username and password. After patient-related information (patient number, date of birth, patient initials) had been entered, the system provided a randomization code for the future use by investigators.

The total treatment period was 70 days starting with the initial diagnosis of high hepatic fat using Magnetic Resonance Imaging Proton Density Fat Fraction (MRI-PDFF) and Magnetic Resonance Spectroscopy (MRS).

For the follow-up visits, the subjects returned to the study center for complete evaluation including body composition analysis and adverse events recording. Hepatic fat content was determined by MR-PDFF on Day 14 and Day 70. Blood samples were obtained for biochemistry, proteomics and metabolomics analyses on Day 0, Day 14 and Day 70. After the Day 70, subjects stopped taking their supplements.

Dosage and Administration

Subjects in active treatment received dietary supplementation with the powder mixture of the four substances. Half dosage of the substances was given for two weeks (one dose taken just after dinner). Then, full dosage (two equal doses taken just after breakfast and dinner) was given for eight weeks.

The dosage of the substances was as follows:

| | Weeks 1-2 (14 days) | Weeks 3-10 (56 days) | |
|---|---|---|---|
| Substance | (g/day) | (g/day) | (mmol/day) |
| Serine | 12.35 | 24.7 | 234 |
| N-Acetylcysteine (NAC) | 2.55 | 5.1 | 31 |

-continued

| | Weeks 1-2 (14 days) | Weeks 3-10 (56 days) | |
|---|---|---|---|
| Substance | (g/day) | (g/day) | (mmol/day) |
| L-Carnitine tartrate | 3.73 | 7.46* | 31 |
| Nicotinamide riboside chloride | 1.00 | 2.00 | 6.9 |

*7.46 g/day L-carnitine tartrate (salt form of L-carnitine) was used to achieve 5.1 g/day of L-carnitine as active ingredient Study Results 56 patients were screened for clinical trial, of whom 32 patients met the eligibility criteria and were randomly assigned to receive treatment. 24 subjects were excluded according to the study protocol. One patient did not initiate the treatment before the randomization due to moving to another city. A total of 20 patients were randomly assigned to the treated group (i.e. the group of subjects taking the mixture of the four substances) and 11 to the placebo group. Another patient was excluded from analysis due to discontinuation during COVID-19 lockdown. 30 of the patients completed the study. However, 8 of the participants were not able to visit the trial site (clinic) for the Day 14 visit due to the COVID-19 lockdown, but completed the final visit on Day 70. The mean age of the patients was 40.4 years (25-63 years) and men accounted for 77.4% of the participants. The baseline demographic and clinical characteristics were not different between the study groups.

The results specifically related to the main aim of the clinical trial, i.e. improvements in NAFLD, are not discussed herein.

However, an analysis of the results of the biochemical tests showed significantly (p=0.00074) reduced serum uric acid levels in the treated group after 14 days (see FIG. 1A). In contrast, no significant reduction was seen in the placebo group (see FIG. 1B).

Figure 2:
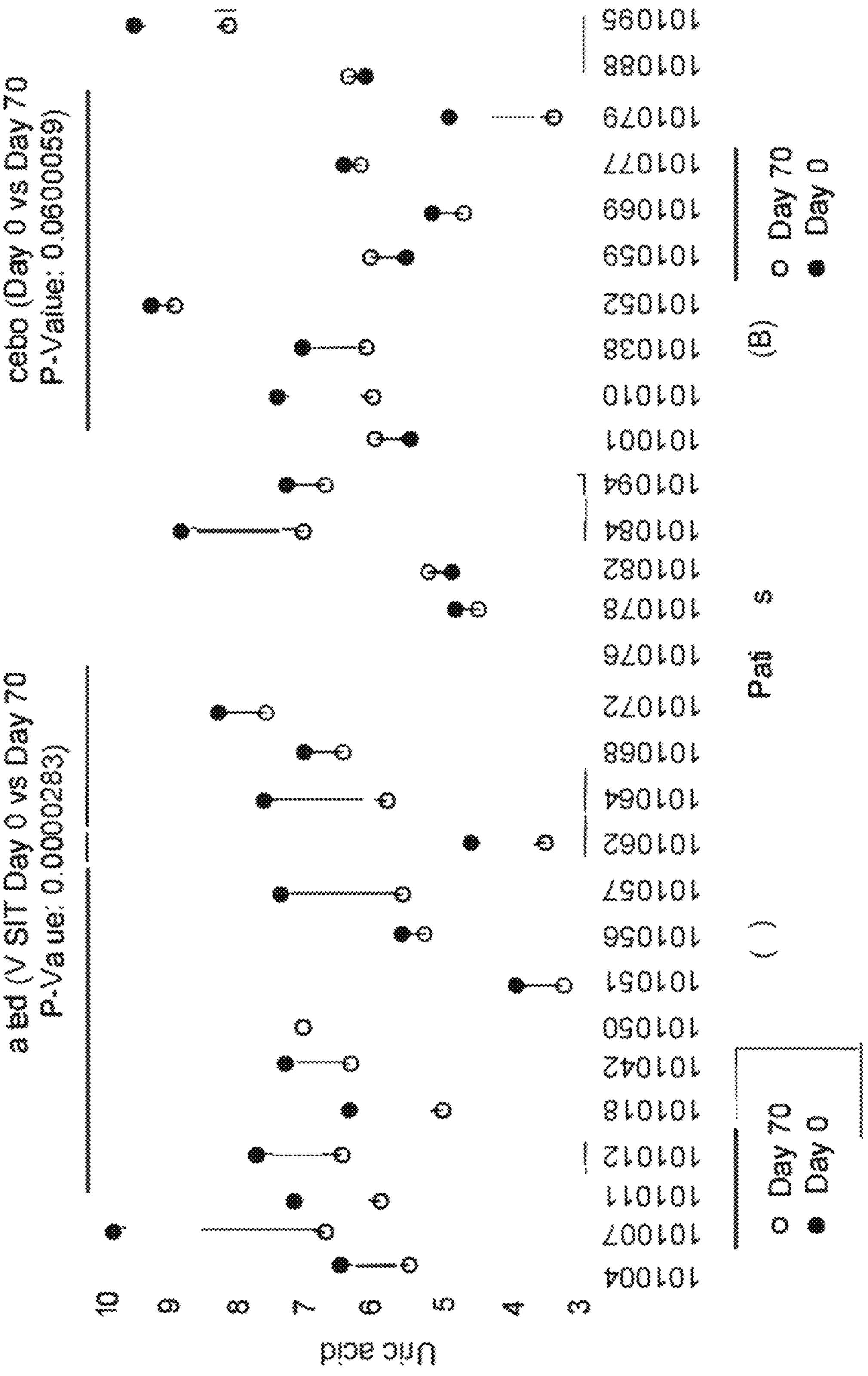
FIG. 2 shows the uric acid levels (mg/dl) at baseline (Day 0) and after ten weeks (Day 70) of oral administration of either the mixture of the four substances (A) or placebo (B).

At the end of the study (Day 70), the reduction in the treated group was even more significant (p=0.000028; see FIG. 2A), whereas there was still no significant reduction in the placebo group (see FIG. 2B).

Figure 3:
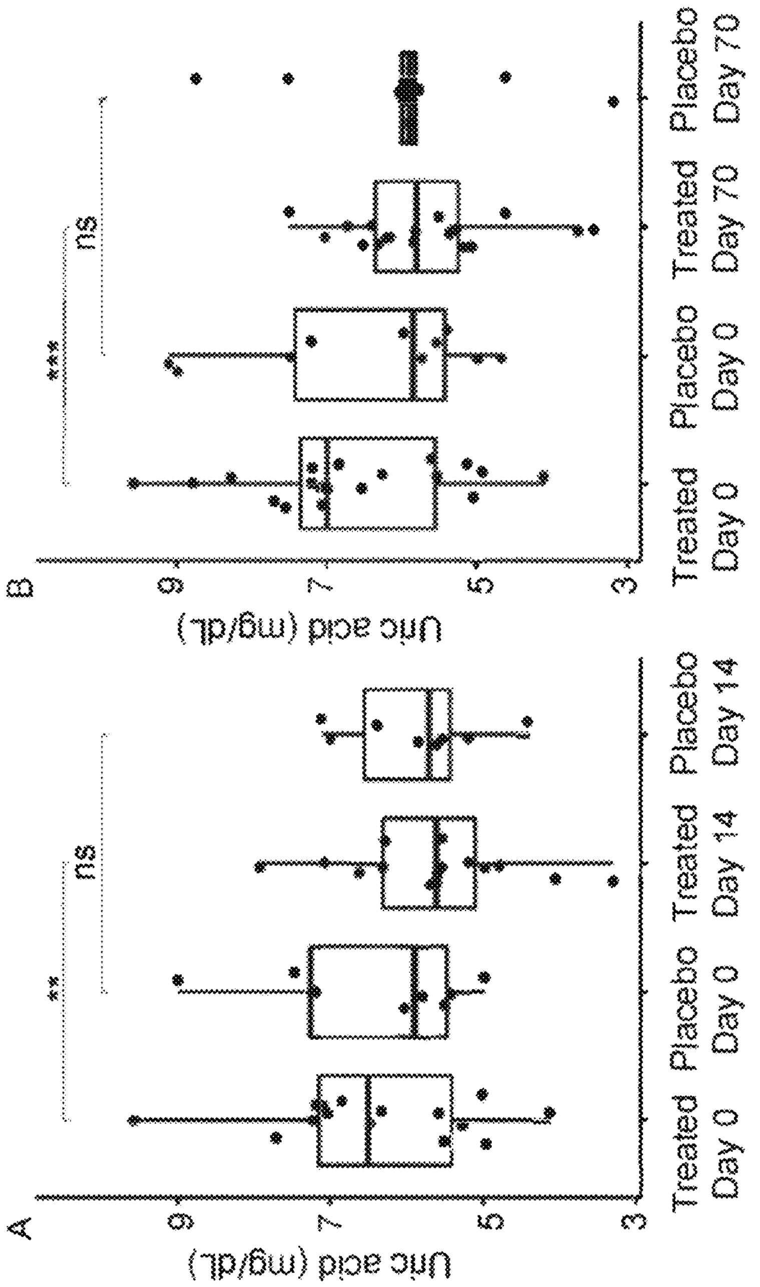
FIG. 3 show box plots of the uric acid levels of the treated group and the placebo group: (A) at baseline (Day 0) and after two weeks (Day 14); and (B) at baseline (Day 0) and after ten weeks (Day 70).

Before taking the mixture of the four substances, the average uric acid serum level in the (to be) treated group was 6.9 mg/dl, which is above the lower limit that commonly defines hyperuricaemia (i.e. 6.8 mg/dl) (see FIGS. 3A and 3B). After taking said mixture, the average uric acid serum level was well below 6.8 mg/dl (see FIGS. 3A and 3B).

Figure 4:
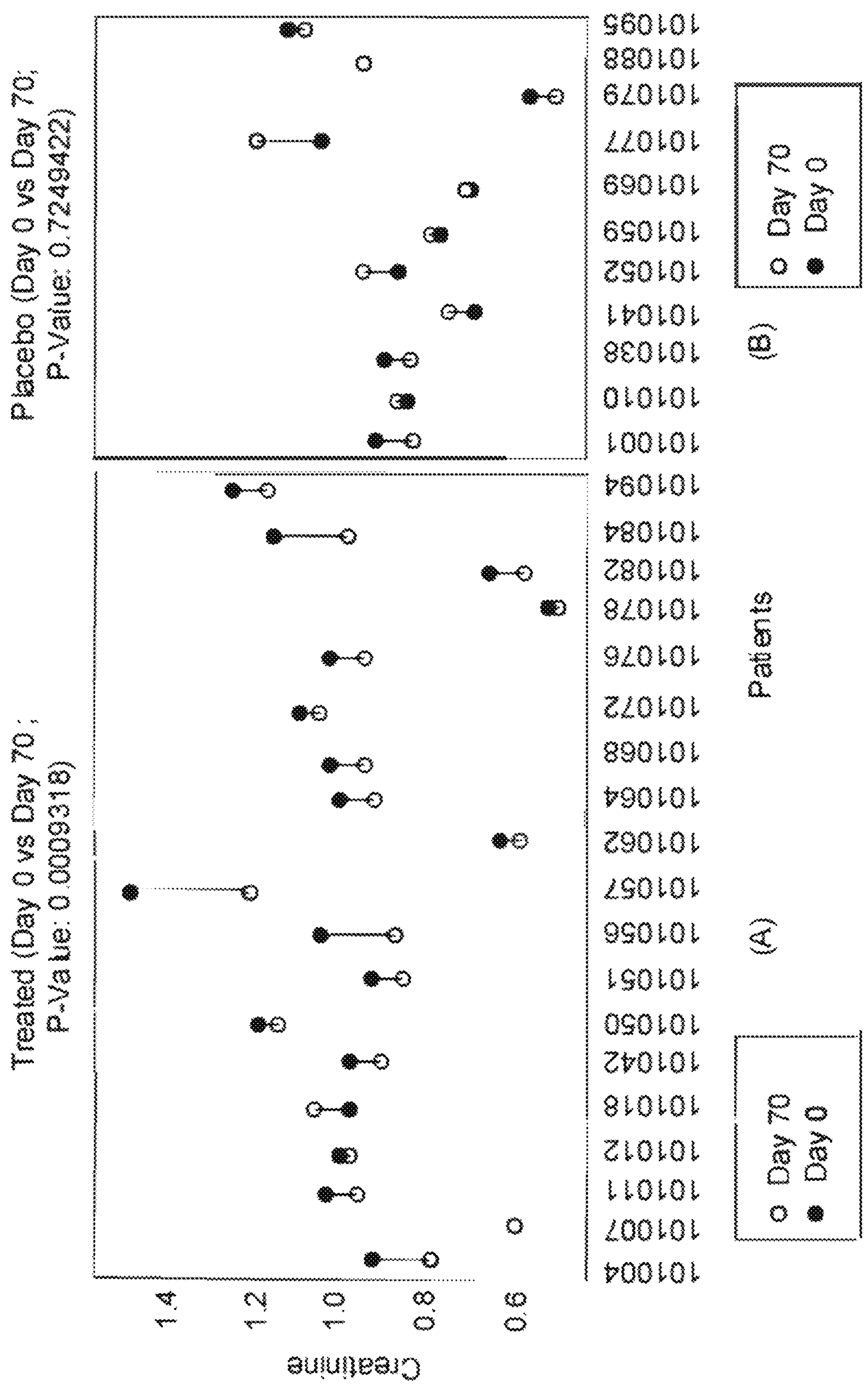
FIG. 4 shows the creatinine levels (mg/dl) at baseline (Day 0) and after ten weeks (Day 70) of oral administration of either the mixture of the four substances (A) or placebo (B).

In the art, serum creatinine is considered to be an indicator of kidney health. Elevated serum creatinine levels have been associated with renal impairment. Hence, it is of relevance to analyse if there was any change in the creatinine levels of in the treated group after taking the mixture of the four substances. FIG. 4A shows significantly (p=0.00093) reduced serum creatinine levels in the treated group after 70 days, hence indicating improved kidney health. In contrast, no significant reduction in serum creatinine levels was observed in the placebo group (see FIG. 4B).

Figure 5:
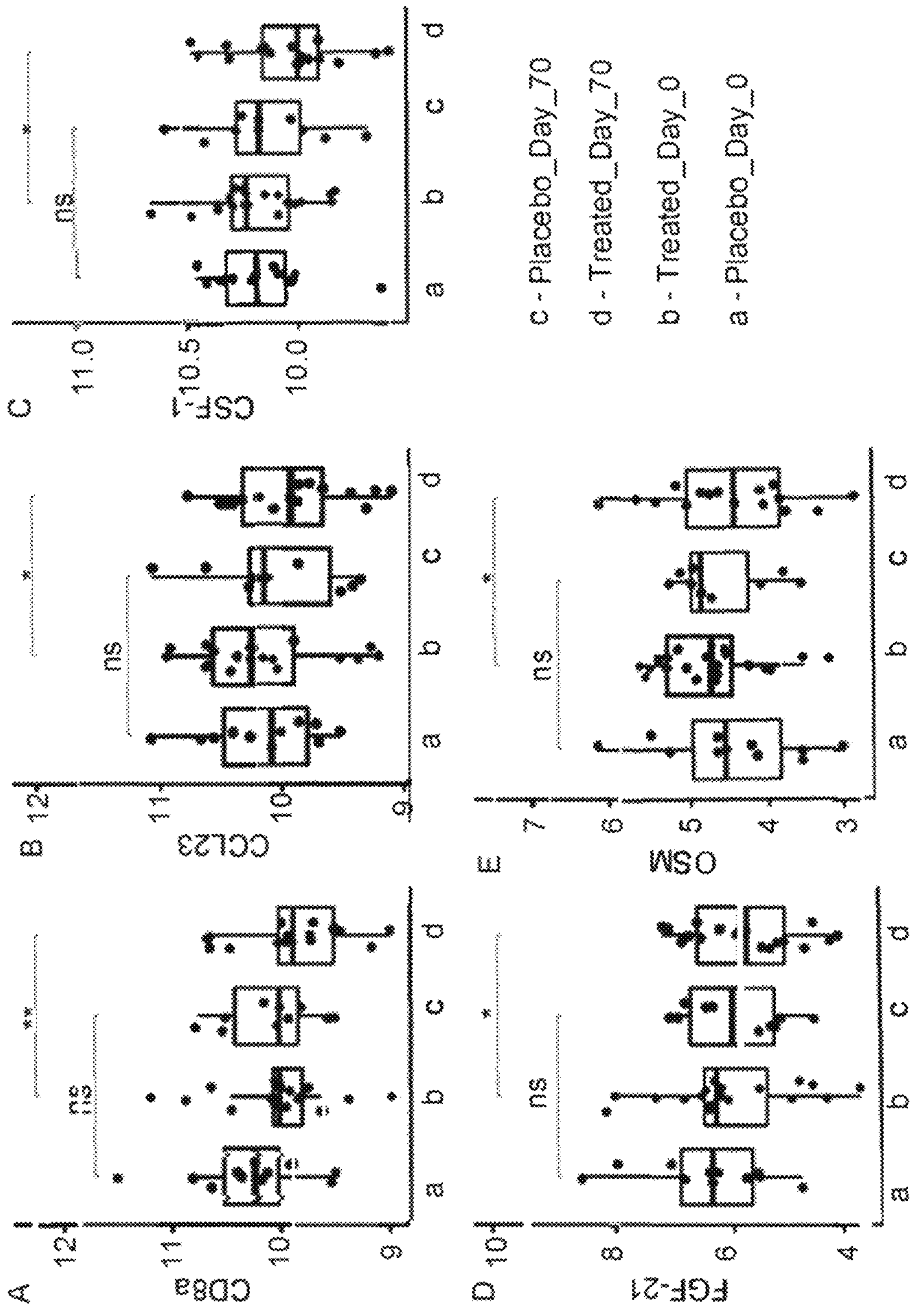
FIG. 5 show box plots of the levels of five different inflammation-related markers in the treated group and the placebo group at baseline (Day 0) and after ten weeks (Day 70). For CD8A, the p-value is 0.0079. For CCL23, the p-value is 0.025. For CSF-1, the p-value is 0.012. For FGF-21, the p-value is 0.038. For OSM, the p-value is 0.048.

Inflammatory proteomics analysis using an Olink Inflammation panel was performed by quantifying the plasma level of 96 proteins. After quality control, filtering out the proteins with missing values in more than 50% of samples, the plasma proteome dataset contained 72 proteins for statistical analysis. It was found that the plasma level of CD8A, CSF-1, CCL23, FGF-21 and OSM, which are associated with inflammation, significantly decreased in the treated group, but not in the placebo group (FIG. 5).

Example: Rat Study

In Vivo Experimental Design

The Ethics Committee of Atatürk University approved all experimental protocols about animal care, handling and experimentation. All experiments were performed in accordance with relevant guidelines and regulations. 44 Sprague Dawley male rats (10-12 weeks old) weighing 375-415 g were obtained from Atatürk University Experimental Research Center (ATADEM) and housed at 22±2° C. with 50±5% humidity on a 12 hr light/dark cycle.

Chow diet (CD) and a high-fat diet (HFD) were used to fed the animals in this study. The CD was composed of wheat, wheat bran, rice polishing and fish meal, with approximately 25% proteins, 60% carbohydrates and 15% fat in terms of the caloric content. On the other hand, HFD was composed of normal food, beef tallow, sugar and condensed milk and contained approximately 14% proteins, 37% carbohydrates and 49% fat in terms of the caloric content.

Following 1-week habituation, the rats were separated into two groups: a control group (Group 1, n=4), which was fed with a regular CD; and the HFD group (n=40), which was fed with HFD. After three weeks, four rats in the HFD group (Group 2) were randomly sacrificed and the remaining 36 rats in the HFD group were randomly divided into nine sub-groups (Groups 3-11, four rats in each subgroup).

Groups 3-11 received the following treatments during weeks four and five:

Group 3 received only the HFD (reference)

Group 4 received the HFD and Serine (1000 mg/kg once daily by oral gavage)

Group 5 received the HFD and NAC (300 mg/kg once daily by oral gavage)

Group 6 received the HFD and L-Carnitine tartrate (LCAT) (100 mg/kg once daily by oral gavage)

Group 7 received the HFD and Nicotinamide riboside chloride (NRCl) (120 mg/kg once daily by oral gavage)

Group 8 received the HFD and Nicotinamide (NA) (120 mg/kg once daily by oral gavage)

Group 9 received the HFD, Serine (1000 mg/kg once daily by oral gavage), NAC (300 mg/kg once daily by oral gavage) and LCAT (100 mg/kg once daily by oral gavage)

Group 10 received the HFD, Serine (1000 mg/kg once daily by oral gavage), NAC (300 mg/kg once daily by oral gavage), LCAT (100 mg/kg/day) and NRCl (120 mg/kg once daily by oral gavage)

Group 11 received the HFD, Serine (1000 mg/kg once daily by oral gavage), NAC (300 mg/kg once daily by oral gavage), LCAT (100 mg/kg once daily by oral gavage) and NA (120 mg/kg once daily by oral gavage)

The body weight and food intake of the rats was recorded each week. After week five, all animals of groups 3-11 were anesthetized with isoflurane and sacrificed. Blood samples were collected from the abdominal aorta and centrifuged at 8000 rpm for 15 min at 4° C. The plasma was separated and stored at −80° C. until further analysis.

Results

Plasma samples were thawed and analyzed for creatinine and uric acid. The results are presented in table 1 below.

TABLE 1

The fold changes of the plasma levels of creatinine and uric acid relative those of group 3 are presented for each of groups 1-2 and 4-11. Significant changes (P < 0.05) are marked with "*".

| Group | Creatinine Fold change | Uric Acid Fold change |
|---|---|---|
| Group 1 (negative control) | 0.59 | 0.43 |
| Group 2 (HFD 3 weeks) | 0.83 | 0.43 |
| Group 3 (HFD reference) | 1.00 | 1.00 |
| Group 4 (HFD + Serine) | 0.84* | 0.72* |
| Group 5 (HFD + NAC) | 0.85 | 0.76 |
| Group 6 (HFD + LCAT) | 0.89 | 0.62* |
| Group 7 (HFD + NRCl) | 0.83* | 0.64* |
| Group 8 (HFD + NA) | 0.96 | 0.53* |
| Group 9 (HFD + Serine, NAC, LCAT) | 0.83 | 0.49* |
| Group 10 (HFD + Serine, NAC, LCAT, NRCl) | 0.81* | 0.51* |
| Group 11 (HFD + Serine, NAC, LCAT, NA) | 0.65* | 0.45* |

Notably, the treatments received by group 10 (Serine, NAC, LCAT, NRCl) and group 11 (HFD+Serine, NAC, LCAT, NA) significantly reduced the levels of creatinine and uric acid. Further, the reductions were greater than those obtained with any of the individual compounds (compare groups 10 and 11 to groups 4-8). The greatest reductions are seen in group 11.

The invention claimed is:

1. A method of lowering the level of uric acid in a subject, comprising administering:

A) serine, glycine, betaine, N-acetylglycine, N-acetylserine, dimethylglycine, sarcosine and/or phosphoserine;

B) N-acetyl cysteine, cysteine, and/or cystine;

C) carnitine, carnitine salt, deoxycarnitine, 4-trimethylammoniobutanal, 3-hydroxy-N6,N6,N6-trimethyl-L-lysine, N6,N6,N6-trimethyl-L-lysine, and/or lysine; and D) nicotinamide riboside, nicotinamide riboside salt, quinolinate, deamino-NAD+, nicotinate D-ribonucleotide, nicotinamide D-ribonucleotide, nicotinate D-ribonucleoside, nicotinamide, and/or nicotinate.

2. The method of claim 1, wherein A), B), C) and D) are administered simultaneously, separately, or sequentially.

3. The method of claim 1, wherein A), B), C) and D) are contained in a composition that is administered to the subject.

4. The method of claim 1, wherein the molar ratio of A) to B) is between 20:1 and 1:4.

5. The method of claim 1, wherein the molar ratio of A) to C) is between 100:1 and 2:1.

6. The method of claim 1, wherein the molar ratio of A) to D) is between 150:1 and 3:1.

7. The method of claim 1, wherein A) is serine, glycine or betaine.

8. The method of claim 1, wherein B) is N-acetyl cysteine or cysteine.

9. The method of claim 1, wherein C) is carnitine.

10. The method of claim 1, wherein D) is nicotinamide riboside or nicotinamide.

11. The method of claim 1, wherein said method comprises orally administering the substances.

12. The method of claim 1, wherein said method comprises administering:

A) in a dose of 0.48-24 mmol/kg/day;

B) in a dose of 0.31-3.05 mmol/kg/day;

C) in a dose of 0.100-2.50 mmol/kg/day; and

D) in a dose of 0.015-0.39 mmol/kg/day.

13. The method of claim 1, wherein said method comprises administering:

A) in a dose of 100-600 mmol/day;

B) in a dose of 12-100 mmol/day;

C) in a dose of 12-100 mmol/day; and

D) in a dose of 3-20 mmol/day.

14. The method of claim 1, wherein A) is L-serine.

15. The method of claim 1, wherein the molar ratio of A) to B) is between 16:1 and 1:4.

16. The method of claim 1, wherein the molar ratio of A) to B) is between 12:1 and 1.5:1.

17. The method of claim 1, wherein the molar ratio of A) to B) is between 10:1 and 3:1.

18. The method of claim 1, wherein the molar ratio of A) to C) is between 30:1 and 3:1.

19. The method of claim 1, wherein the molar ratio of A) to D) is between 90:1 and 10:1.

20. The method of claim 12, wherein said method comprises administering:

A) in a dose of 1.8-4.8 mmol/kg/day;

B) in a dose of 0.40-1.23 mmol/kg/day;

C) in a dose of 0.230-1.00 mmol/kg/day; and

D) in a dose of 0.040-0.20 mmol/kg/day.

21. The method of claim 13, wherein said method comprises administering:

A) in a dose of 150-450 mmol/day;

B) in a dose of 16-75 mmol/day;

C) in a dose of 16-75 mmol/day; and

D) in a dose of 3-15 mmol/day.

22. The method of claim 1, wherein the carnitine salt is a carnitine tartrate.

23. The method of claim 22, wherein the carnitine tartrate is an L-carnitine tartrate.

24. The method of claim 1, wherein the nicotinamide riboside salt is a nicotinamide riboside chloride.

25. A method of treating hyperuricaemia in a subject, comprising administering:

A) serine, glycine, betaine, N-acetylglycine, N-acetylserine, dimethylglycine, sarcosine and/or phosphoserine;

B) N-acetyl cysteine, cysteine, and/or cystine;

C) carnitine, carnitine salt, deoxycarnitine, 4-trimethylammoniobutanal, 3-hydroxy-N6,N6,N6-trimethyl-L-lysine, N6,N6,N6-trimethyl-L-lysine, and/or lysine; and D) nicotinamide riboside, nicotinamide riboside salt, quinolinate, deamino-NAD+, nicotinate D-ribonucleotide, nicotinamide D-ribonucleotide, nicotinate D-ribonucleoside, nicotinamide, and/or nicotinate.

26. A method of treating gout in a subject, comprising administering:

A) serine, glycine, betaine, N-acetylglycine, N-acetylserine, dimethylglycine, sarcosine and/or phosphoserine;

B) N-acetyl cysteine, cysteine, and/or cystine;

C) carnitine, carnitine salt, deoxycarnitine, 4-trimethylammoniobutanal, 3-hydroxy-N6,N6,N6-trimethyl-L-lysine, N6,N6,N6-trimethyl-L-lysine, and/or lysine; and D) nicotinamide riboside, nicotinamide riboside salt, quinolinate, deamino-NAD+, nicotinate D-ribonucleotide, nicotinamide D-ribonucleotide, nicotinate D-ribonucleoside, nicotinamide, and/or nicotinate.

* * * * *